(12) United States Patent
Field et al.

(10) Patent No.: US 11,656,119 B2
(45) Date of Patent: *May 23, 2023

(54) HIGH DENSITY OPTICAL MEASUREMENT SYSTEMS WITH MINIMAL NUMBER OF LIGHT SOURCES

(71) Applicant: HI LLC, Los Angeles, CA (US)

(72) Inventors: Ryan Field, Culver City, CA (US); Husam Katnani, Braintree, MA (US); Katherine Perdue, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/508,325

(22) Filed: Oct. 22, 2021

(65) Prior Publication Data
US 2022/0042843 A1 Feb. 10, 2022

Related U.S. Application Data

(63) Continuation of application No. 17/202,641, filed on Mar. 16, 2021, now Pat. No. 11,187,575.
(Continued)

(51) Int. Cl.
*G01J 1/02* (2006.01)
*G01J 1/04* (2006.01)

(52) U.S. Cl.
CPC ............ *G01J 1/0219* (2013.01); *G01J 1/0238* (2013.01); *G01J 1/0422* (2013.01)

(58) Field of Classification Search
CPC ...... G01J 1/0219; G01J 1/0238; G01J 1/0422; A61B 5/6803; A61B 5/0059;
(Continued)

(56) References Cited

U.S. PATENT DOCUMENTS 5,088,493 A * 2/1992 Giannini ............... A61B 5/0059
600/323
5,853,370 A 12/1998 Chance et al.
(Continued)

FOREIGN PATENT DOCUMENTS

| KR | 20170087639 A | 7/2017 |
|---|---|---|
| WO | 2018033751 | 2/2018 |
| WO | 2019221784 A1 | 11/2019 |

OTHER PUBLICATIONS

International Search Report and Written Opinion dated Sep. 6, 2021 in corresponding International Application No. PCT/US21/22488 with International Filing Date of Mar. 16, 2021.
(Continued)

*Primary Examiner* — Sang H Nguyen
(74) *Attorney, Agent, or Firm* — ALG Intellectual Property, LLC

(57) ABSTRACT

An illustrative optical measurement system may include a wearable assembly comprising a plurality of modules each configured to fit within a different slot of the wearable assembly. The plurality of modules may include a module that comprises first and second light sources each configured to emit light directed at a target and a set of detectors configured to detect arrival times for photons of the light emitted by the first and second light sources. A ratio of a total number of the detectors to a total number of the light sources is at least two to one.

14 Claims, 24 Drawing Sheets

Related U.S. Application Data

(60) Provisional application No. 63/052,609, filed on Jul. 16, 2020, provisional application No. 62/992,516, filed on Mar. 20, 2020.

(58) Field of Classification Search
CPC .......... A61B 5/4064; A61B 2562/0238; A61B 2560/0443; G01S 17/10; G01S 17/88; G01S 7/4815; G01S 7/4863
See application file for complete search history.

(56) References Cited

U.S. PATENT DOCUMENTS

| | | | |
|---|---|---|---|
| 6,240,309 | B1 | 5/2001 | Yamashita et al. |
| 6,384,663 | B2 | 5/2002 | Cova et al. |
| 6,640,133 | B2 | 10/2003 | Yamashita |
| 6,683,294 | B1 | 1/2004 | Herbert et al. |
| 7,356,365 | B2 | 4/2008 | Schurman |
| 7,547,872 | B2 | 6/2009 | Niclass et al. |
| 7,774,047 | B2 | 8/2010 | Yamashita et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,633,431 | B2 | 1/2014 | Kim |
| 8,817,257 | B2 | 8/2014 | Herve |
| 9,058,081 | B2 | 6/2015 | Baxter |
| 9,076,707 | B2 | 7/2015 | Harmon |
| 9,131,861 | B2 | 9/2015 | Ince et al. |
| 9,316,735 | B2 | 4/2016 | Baxter |
| 9,401,448 | B2 | 7/2016 | Bienfang et al. |
| 9,419,635 | B2 | 8/2016 | Kumar et al. |
| 9,442,201 | B2 | 9/2016 | Schmand et al. |
| 9,529,079 | B1 | 12/2016 | Droz |
| 9,574,936 | B2 | 2/2017 | Heinonen |
| 9,634,826 | B1 | 4/2017 | Park |
| 9,946,344 | B2 | 4/2018 | Ayaz et al. |
| D817,553 | S | 5/2018 | Aaskov et al. |
| 9,997,551 | B2 | 6/2018 | Mandai et al. |
| D825,112 | S | 8/2018 | Saez |
| 10,158,038 | B1 | 12/2018 | Do Valle et al. |
| 10,340,408 | B1 | 7/2019 | Katnani |
| 10,424,683 | B1 | 9/2019 | Do Valle |
| 10,515,993 | B2 | 12/2019 | Field et al. |
| 10,697,829 | B2 | 6/2020 | Delic |
| 10,772,561 | B2 | 9/2020 | Donaldson |
| 10,809,796 | B2 | 10/2020 | Armstrong-Muntner |
| 10,912,504 | B2 | 2/2021 | Nakaji |
| 11,006,876 | B2 | 5/2021 | Johnson |
| 11,006,878 | B2 | 5/2021 | Johnson |
| 2005/0038344 | A1* | 2/2005 | Chance ................ A61B 5/0073 600/476 |
| 2005/0228291 | A1* | 10/2005 | Chance ................ A61B 5/0042 600/407 |
| 2007/0038116 | A1* | 2/2007 | Yamanaka ............. G01N 21/49 600/476 |
| 2007/0083097 | A1 | 4/2007 | Fujiwara |
| 2009/0012402 | A1 | 1/2009 | Mintz |
| 2009/0054789 | A1 | 2/2009 | Kiguchi et al. |
| 2011/0208675 | A1 | 8/2011 | Shoureshi et al. |
| 2012/0016635 | A1 | 1/2012 | Brodsky et al. |
| 2012/0083673 | A1 | 4/2012 | Al-Ali et al. |
| 2013/0030270 | A1 | 1/2013 | Chiou et al. |
| 2013/0090541 | A1 | 4/2013 | MacFarlane et al. |
| 2013/0225953 | A1 | 8/2013 | Oliviero et al. |
| 2013/0342835 | A1 | 12/2013 | Blacksberg |
| 2014/0171757 | A1 | 6/2014 | Kawato et al. |
| 2014/0191115 | A1 | 7/2014 | Webster et al. |
| 2014/0217264 | A1 | 8/2014 | Shepard |
| 2014/0275891 | A1 | 9/2014 | Muehlemann et al. |
| 2015/0038811 | A1 | 2/2015 | Asaka |
| 2015/0038812 | A1 | 2/2015 | Ayaz et al. |
| 2015/0041625 | A1 | 2/2015 | Dutton |
| 2015/0054111 | A1 | 2/2015 | Niclass et al. |
| 2015/0057511 | A1* | 2/2015 | Basu .................... A61B 5/6826 600/475 |
| 2015/0077279 | A1 | 3/2015 | Song |
| 2015/0150505 | A1 | 6/2015 | Kaskoun et al. |
| 2015/0157262 | A1 | 6/2015 | Schuessler |
| 2015/0157435 | A1 | 6/2015 | Chasins et al. |
| 2015/0327777 | A1 | 11/2015 | Kostic et al. |
| 2015/0364635 | A1 | 12/2015 | Bodlovic et al. |
| 2016/0296168 | A1 | 10/2016 | Abreu |
| 2017/0030769 | A1 | 2/2017 | Clemens et al. |
| 2017/0052065 | A1 | 2/2017 | Sharma et al. |
| 2017/0085547 | A1 | 3/2017 | De Aguiar et al. |
| 2017/0176596 | A1 | 6/2017 | Shpunt et al. |
| 2017/0179173 | A1 | 6/2017 | Mandai et al. |
| 2017/0202518 | A1 | 7/2017 | Furman et al. |
| 2017/0281086 | A1 | 10/2017 | Donaldson |
| 2017/0363467 | A1 | 12/2017 | Clemens et al. |
| 2017/0367650 | A1 | 12/2017 | Wallois |
| 2018/0014741 | A1 | 1/2018 | Chou |
| 2018/0020960 | A1* | 1/2018 | Sarussi ............... G01N 33/4925 600/310 |
| 2018/0027196 | A1 | 1/2018 | Yang et al. |
| 2018/0039053 | A1 | 2/2018 | Kremer et al. |
| 2018/0066986 | A1 | 3/2018 | Kasai et al. |
| 2018/0070830 | A1 | 3/2018 | Sutin et al. |
| 2018/0070831 | A1 | 3/2018 | Sutin et al. |
| 2018/0089848 | A1 | 3/2018 | Yang et al. |
| 2018/0103861 | A1* | 4/2018 | Sutin ..................... A61B 5/318 |
| 2018/0120152 | A1 | 5/2018 | Leonardo |
| 2018/0180473 | A1 | 6/2018 | Clemens et al. |
| 2019/0113385 | A1 | 4/2019 | Fukuchi |
| 2019/0120975 | A1 | 4/2019 | Ouvrier-Buffet |
| 2019/0175068 | A1 | 6/2019 | Everdell |
| 2019/0209012 | A1 | 7/2019 | Yoshimoto et al. |
| 2019/0355861 | A1 | 11/2019 | Katnani |
| 2019/0363210 | A1 | 11/2019 | Do Valle |
| 2019/0388018 | A1 | 12/2019 | Horstmeyer |
| 2020/0060542 | A1 | 2/2020 | Alford |
| 2020/0116838 | A1 | 4/2020 | Erdogan |
| 2020/0136632 | A1 | 4/2020 | Lin |
| 2020/0188030 | A1 | 6/2020 | Kopper et al. |
| 2020/0196932 | A1 | 6/2020 | Johnson et al. |
| 2020/0253479 | A1 | 8/2020 | Nurmikko |
| 2020/0315510 | A1 | 10/2020 | Johnson |
| 2020/0337624 | A1 | 10/2020 | Johnson |
| 2020/0390358 | A1 | 12/2020 | Johnson |
| 2021/0265512 | A1 | 8/2021 | Ayel |
| 2021/0290064 | A1 | 9/2021 | Do Valle |
| 2021/0294996 | A1 | 9/2021 | Field |

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680.

Ban, et al., "Kernel Flow: a high channel count scalable TD-fNIRS system", https://www.spiedigitallibrary.org/conference-proceedings-of-spie Proc. of SPIE vol. 11663, 116630B CCC code: 1605-7422/21/$21 doi: 10.1117/12.2582888.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed. Opt. Express 11(11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Huppert, et al., "HomER: a review of time-series analysis methods for near-infrared spectroscopy of the brain", Appl Opt. 48(10), D280 (2009).

Kienle, et al., "Improved solutions of the steady-state and the time-resolved diffusion equations for reflectance from a semi-infinite turbid medium", J. Opt. Soc. Am. A 14(1), 246 (1997).

Konugolu, et al., "Broadband (600-1350 nm) Time-Resolved Diffuse Optical Spectrometer for Clinical Use", IEEE Journal of

(56) References Cited

OTHER PUBLICATIONS

Selected Topics in Quantum Electronics, vol. 22, No. 3, May/Jun. 2016.
Lacerenza, et al., "Wearable and wireless time-domain near-infrared spectroscopy system for brain and muscle hemodynamic monitoring", Biomed. Opt. Express 11(10), 5934 (2020).
Lange, et al., "Clinical Brain Monitoring with Time Domain NIRS: A Review and Future Perspectives", Applied Sciences 9(8), 1612(2019).
Lange, et al., "Maestros: A Multiwavelength Time-Domain NIRS System to Monitor Changes in Oxygenation and Oxidation State of Cytochrome-C-Oxidase", IEEE J. Select Topics Quantum Electron. 25(1), 1-12 (2019).
Martelli, et al., "Optimal estimation reconstruction of the optical properties of a two-layered tissue phantom from time-resolved single-distance measurements", Journal of Biomedical Optics 20(11), 115001 (Nov. 2015).
Mora, et al., "Fast silicon photomultiplier improves signal harvesting and reduces complexity in time-domain diffuse optics", Opt. Express 23(11), 13937 (2015).
Pifferi, et al., "Performance assessment of photon migration instruments: the MEDPHOT protocol", Applied Optics, 44(11), 2104-2114.
Prahl, et al., "Optical Absorption of Hemoglobin", http://omlc.ogi.edu/spectra/hemoglobin/index.html.
Re, et al., "Multi-channel medical device for time domain functional near infrared spectroscopy based on wavelength space multiplexing", Biomed Opt. Express 4(10), 2231 (2013).
Renna, et al., "Eight-Wavelength, Dual Detection Channel Instrument for Near-Infrared Time-Resolved Diffuse Optica Spectroscopy", IEEE J. Select. Topics Quantum Electron. 25(1), 1-11 (2019).
Torricelli, et al., "Time domain functional NIRS imaging for human brain mapping", NeuroImage 85, 28-50 (2014).
Wabniiz, et al., "Depth-selective data analysis for time-domain fNIRS: moments vs. time windows", Biomed. Opt. Express 11(8), 4224 (2020).
Wabnitz, et al., "Performance assessment of time-domain optical brain imagers, part 1: basic instrumental performance protocol", Journal of Biomedical Optics 19(8), 086010 (Aug. 2014).
Wabnitz, et al., "Performance assessment of time-domain optical brain imagers, part 2: nEUROPt protocol", Journal of Biomedical Optics 19(8), 086012 (Aug. 2014).
Wojtkiewicz, et al., "Self-calibrating time-resolved near infrared spectroscopy", Biomed. Opt. Express 10(5), 2657 (2019).
Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893.
Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi: 10.3390/s18113680, Oct. 29, 2018.
Ban, et al., "Kernel Flow: a high channel count scalable TD-fNIRS system", https://www.spiedigitallibrary.org/conference-proceedings-of-spie Proc. of SPIE vol. 11663, 116630B CCC code: 1605-7422/21/321 doi: 10.1117/12.2582888, Mar. 5, 2021.
Lange, et al., "MAESTROS: A Multwavelength Time-Domain NIRS System to Monitor Changes in Oxygenation and Oxidation State of Cytochrome-C-Oxidase", IEEE J. Select. Topics Quantum Electron. 25(1), 1-12 (2019).
Pifferi, et al., "Performance assessment of photon migration instruments: the MEDPHOT protocol", Applied Optics, 44(11), 2104-2114 (2005).
Prahl, et al., "Optical Absorption of Hemoglobin", http://omic.ogi.edu/spectra/hemoglobin/index.html (1999).
Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).
Wabnitz, et al., "Depth-selective data analysis for time-domain fNIRS: moments vs. time windows", Biomed. Opt. Express 11(8), 4224 (2020).
Wojtkiewicz, et al., "Seif-calibrating time-resolved near infrared spectroscopy", Biomed. Opt. Express 10(5), 2657 (2019).
"International Preliminary Report on Patentability, mailed in International Application PCT/US2021/022488 dated Sep. 29, 2022".

* cited by examiner

HIGH DENSITY OPTICAL MEASUREMENT SYSTEMS WITH MINIMAL NUMBER OF LIGHT SOURCES

RELATED APPLICATIONS

The present application is a continuation of U.S. patent application Ser. No. 17/202,641, filed on Mar. 16, 2021, which claims priority under 35 U.S.C. § 119(e) to U.S. Provisional Patent Application No. 62/992,516, filed on Mar. 20, 2020, and to U.S. Provisional Patent Application No. 63/052,609, filed on Jul. 16, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

High density optical measurement systems with a minimal number of light sources are described herein. For example, an optical measurement system may include a wearable assembly configured to be worn by a user and including a plurality of light sources each configured to emit light directed at a target and a plurality of detectors configured to detect arrival times for photons of the light after the light is scattered by the target. A ratio of a total number of the detectors to a total number of the light sources is at least two to one.

As described herein, a physical positioning of the detectors and light sources within the wearable assembly may result in both spatial and temporal overlapping of light source/detector pairs (also referred to herein as "S-D pairs"), where the same light source is included in more than one S-D pair. This, together with the time-of-flight measurement techniques described herein, may result in optical measurements that have an effective spatial resolution that is relatively high even without a dedicated light source for every detector, as is found in conventional high density digital optical tomography (HD DOT) systems.

These and other advantages and benefits of the present systems, circuits, and methods are described more fully herein.

Figure 1:
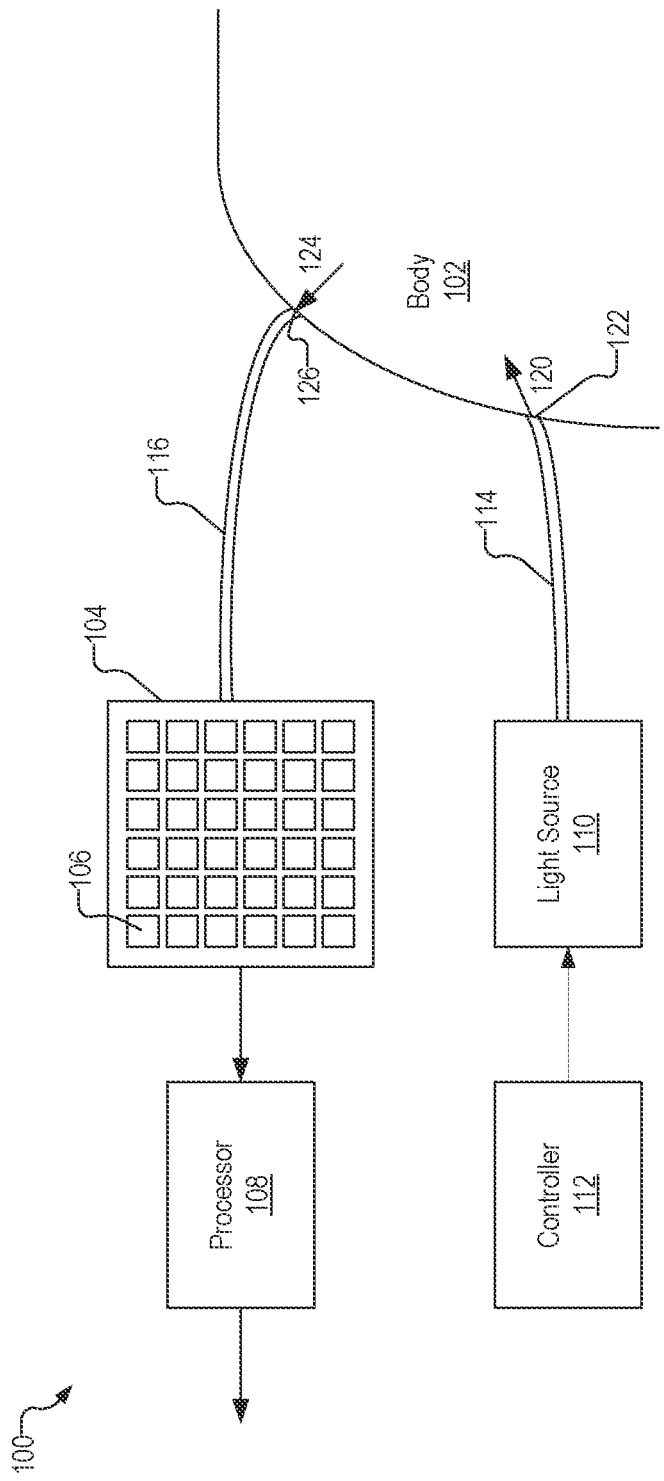
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique (e.g., a time-of-flight measurement technique). Example time domain-based optical measurement techniques include, but are not limited to, TCSPC, time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2" photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (m LEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
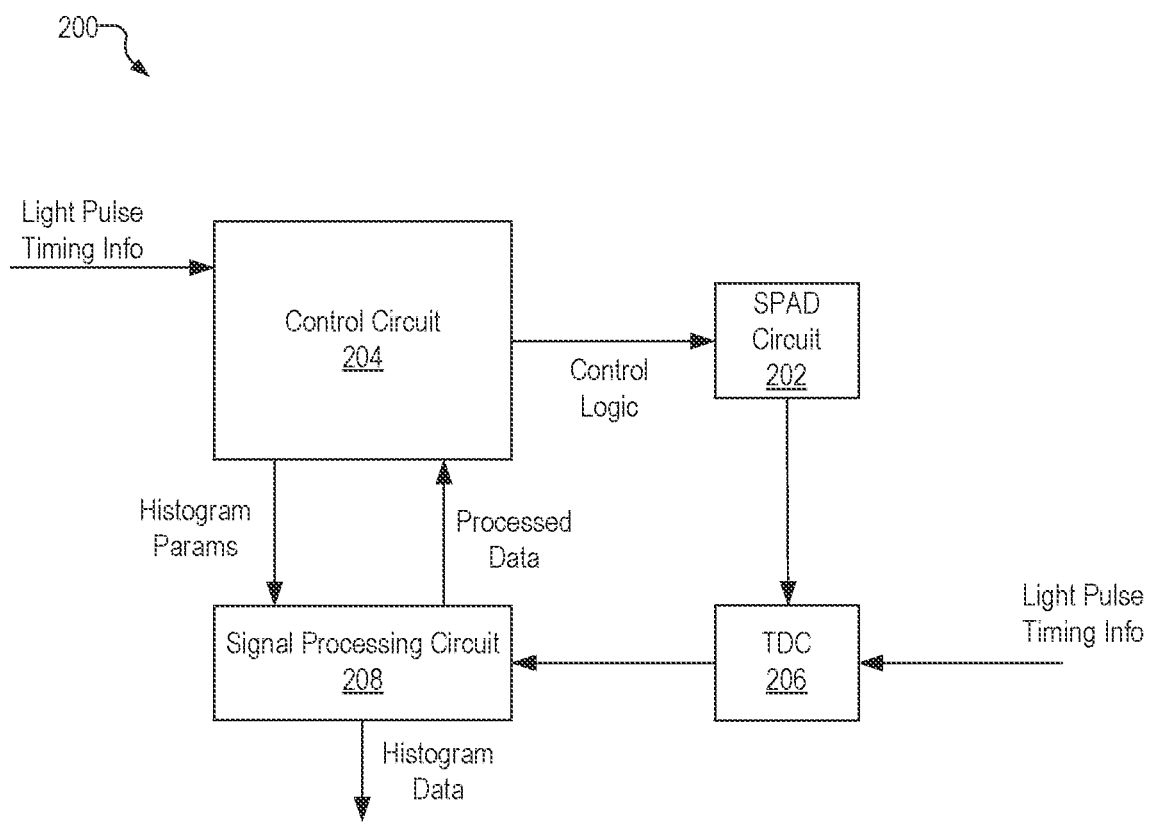
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their respective entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 202). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
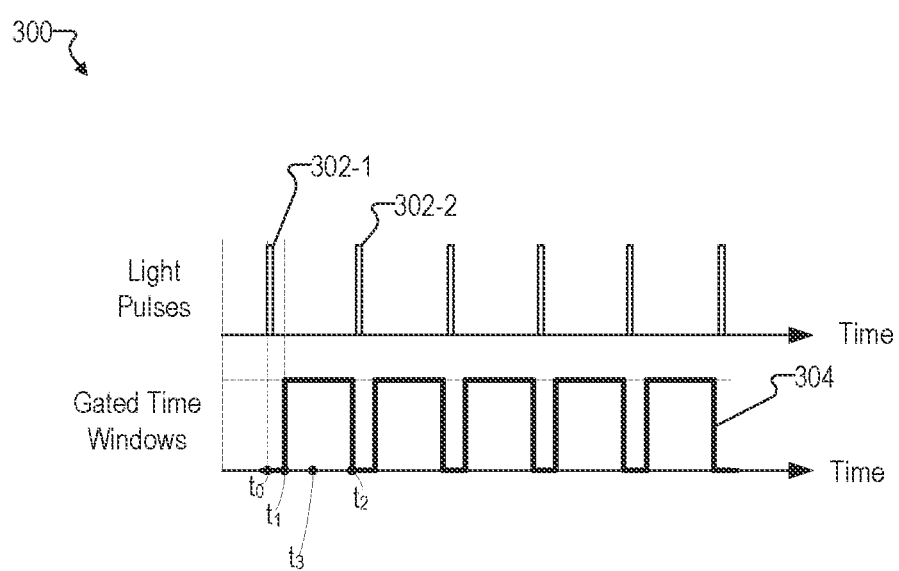
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time $t_0$. At a time a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors.

Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
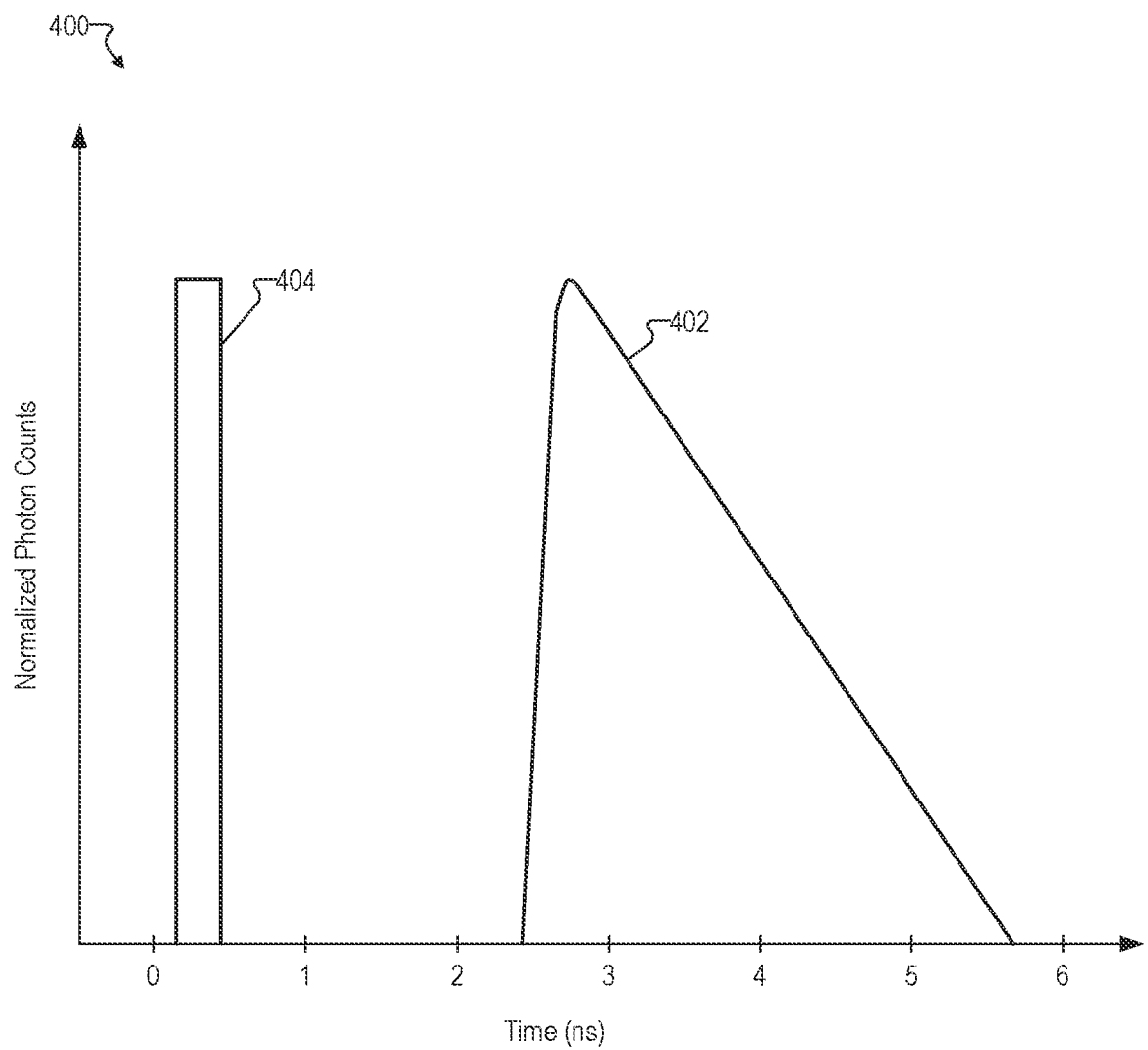
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
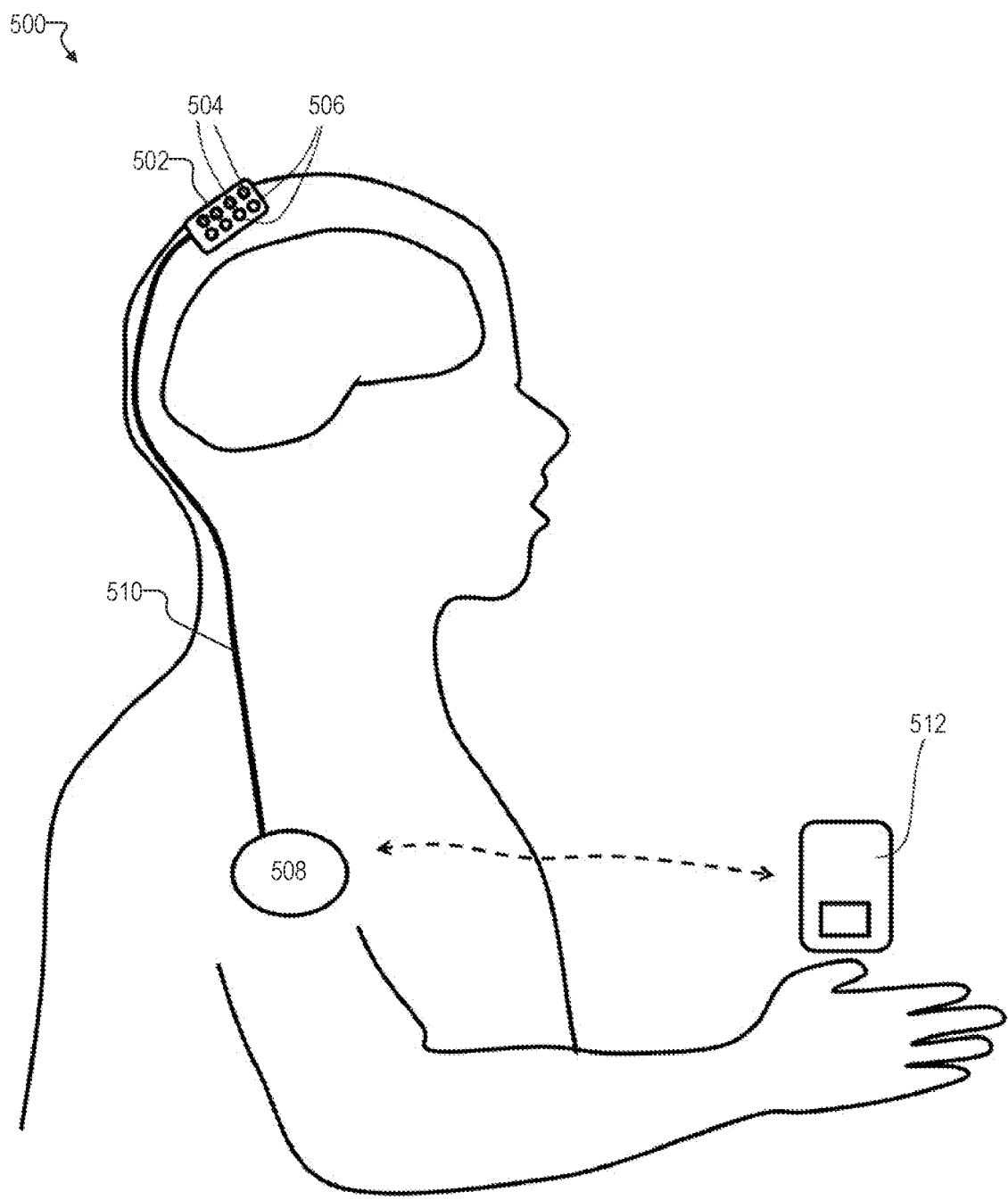
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Figure 6:
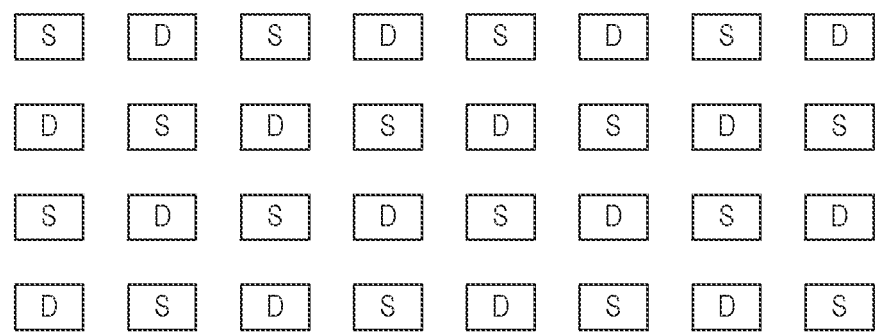
FIG. 6 shows a high density digital optical tomography system.

A conventional HD DOT system is characterized by a regular grid of light sources and detectors (e.g., photodetectors). For example, FIG. 6 shows an HD DOT system 600 that includes a grid of alternating light sources (labeled "S") and detectors (labeled "D") such that a ratio of light sources to detectors is one to one. This provides a relatively high number of overlapping S-D pairs, which means that light from a particular light source can be detected by multiple detectors that are located near the light source. This may provide relatively high density spatial information. However, such a configuration disadvantageously requires a relatively high number of light sources, which can make the HD DOT system 600 physically large and/or consume a relatively high amount of power.

Figure 7:
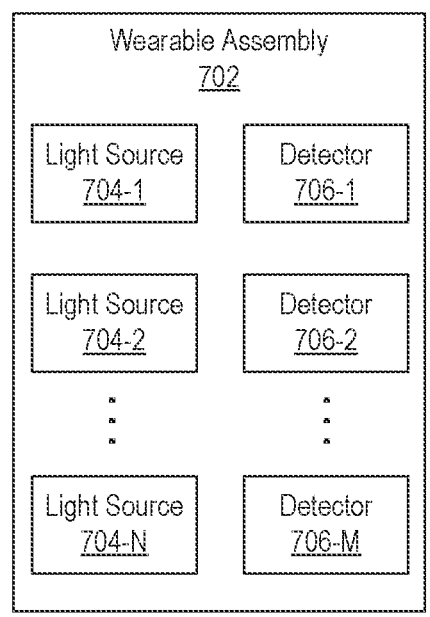
FIG. 7 shows an exemplary optical measurement system.

In contrast, FIG. 7 shows an exemplary optical measurement system 700 in accordance with the principles described herein. Optical measurement system 700 may be an implementation of optical measurement system 100 and, as shown, includes a wearable assembly 702, which includes N light sources 704 (e.g., light sources 704-1 through 704-N) and M detectors 706 (e.g., detectors 706-1 through 706-M). Optical measurement system 700 may include any of the other components of optical measurement system 100 as may serve a particular implementation.

Light sources 704 are each configured to emit light and may be implemented by any of the light sources described herein. Detectors 706 may each be configured to detect arrival times for photons of the light emitted by one or more light sources 704 after the light is scattered by the target. For example, a detector 706 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon.

Wearable assembly 702 may be implemented by any of the wearable devices, wearable module assemblies, and/or wearable units described herein. For example, wearable assembly 702 may be implemented by a wearable device configured to be worn on a user's head. Wearable assembly 702 may additionally or alternatively be configured to be worn on any other part of a user's body.

In accordance with the principles described herein, a ratio of the total number of detectors 706 (i.e., M) to the total number of light sources (i.e., N) is at least two to one. In other words, there are at least twice as many detectors in wearable assembly 702 as there are light sources.

As described herein, a physical positioning of detectors 706 and light sources 704 within wearable assembly 702 may result in both spatial and temporal overlapping of S-D pairs, where the same light source is included in more than one S-D pair. This, in combination with the time-of-flight measurement techniques described herein, may result in optical measurements that have an effective spatial resolution that is relatively high even without a dedicated light source for every detector, as is found in conventional HD DOT systems (e.g., HD DOT system 600 shown in FIG. 6). This in turn allows for the implementations of optical measurement system 700 described to have fewer light sources and/or detectors than conventional HD DOT systems while still having at least the same effective spatial resolution.

Optical measurement system 700 may be modular in that one or more components of optical measurement system 700 may be removed, changed out, or otherwise modified as may serve a particular implementation. As such, optical measurement system 700 may be configured to conform to three-dimensional surface geometries, such as a user's head. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

To illustrate, various modular assemblies that implement optical measurement system 700 are described in connection with FIGS. 8-14. The modular assemblies described herein are merely illustrative of the many different implementations of optical measurement system 700 that may be realized in accordance with the principles described herein. Each of the modular assemblies described herein may include one or more modules and may be worn on the head or any other suitable body part of the user.

In FIGS. 8-14, the illustrated modules may, in some examples, be physically distinct from each other. For example, as described herein, each module may be configured to be removably attached to a wearable assembly (e.g., by being inserted into a different slot of the wearable assembly). This may allow the modular assemblies to conform to three-dimensional surface geometries, such as a user's head.

In FIGS. 8-14, each illustrated module may include one or more light sources labeled "S" and a set of detectors each labeled "D". Some specific light sources and detectors are also referred to by specific reference numbers. Each light source depicted in FIGS. 8-14 may be implemented by one or more light sources similar to light source 110 and may be configured to emit light directed at a target (e.g., the brain). Each detector depicted in FIGS. 8-14 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

Figure 8:
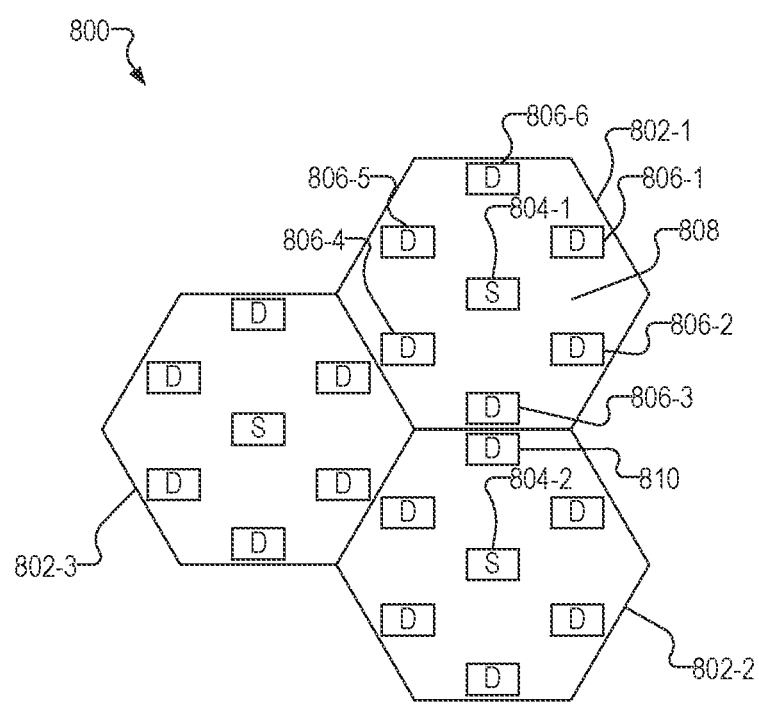
FIGS. 8-14 illustrate various modular assemblies that may implement one or more of the optical measurement systems described herein.

FIG. 8 shows an illustrative modular assembly 800 that may implement optical measurement system 700. As shown, modular assembly 800 includes a plurality of modules 802 (e.g., modules 802-1 through 802-3). While three modules 802 are shown to be included in modular assembly 800, in alternative configurations, any number of modules 802 (e.g., a single module up to sixteen or more modules) may be included in modular assembly 800.

Each module 802 includes a light source (e.g., light source 804-1 of module 802-1 and light source 804-2 of module 802-2) and a plurality of detectors (e.g., detectors 806-1 through 806-6 of module 802-1). In the particular implementation shown in FIG. 8, each module 802 includes a single light source and six detectors such that a ratio of detectors to light sources in modular assembly 800 is six to one.

Each light source (e.g., light source 804-1 or light source 804-2) depicted in FIG. 8 may be located at a center region of a surface of the light source's corresponding module. For example, light source 804-1 is located at a center region of a surface 808 of module 802-1. In alternative implementations, a light source of a module may be located away from a center region of the module.

The detectors of a module may be distributed around the light source of the module. For example, detectors 806 of module 802-1 are distributed around light source 804-1 on surface 808 of module 802-1. In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 9A:
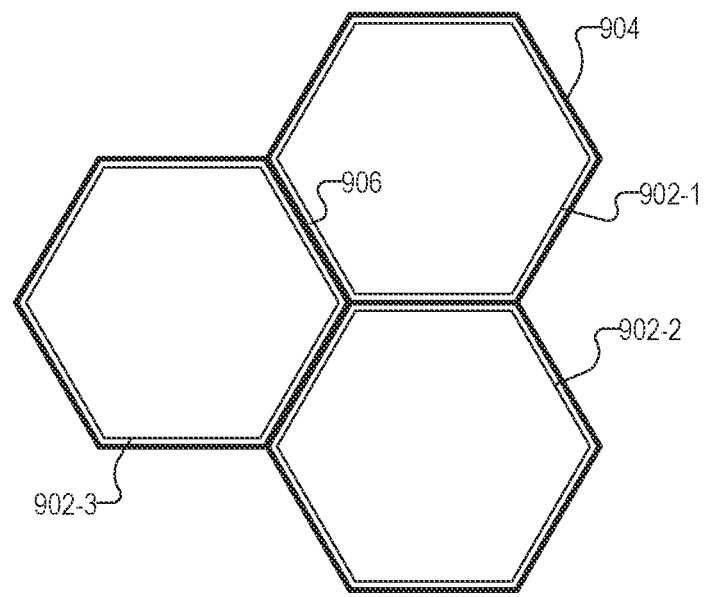
Figure 9B:
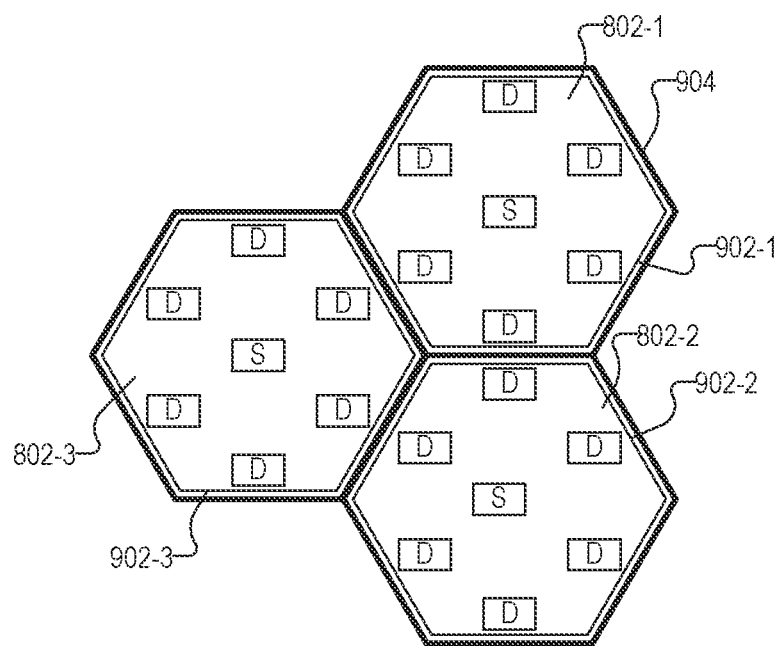

In FIG. 8, modules 802 are shown to be adjacent to and touching one another. Modules 802 may alternatively be spaced apart from one another. For example, FIGS. 9A-9B show an exemplary implementation of modular assembly 800 in which modules 802 are configured to be inserted into individual slots 902 (e.g., slots 902-1 through 902-3, also referred to as cutouts) of a wearable assembly 904. In particular, FIG. 9A shows the individual slots 902 of the wearable assembly 904 before modules 802 have been inserted into respective slots 902, and FIG. 9B shows wearable assembly 904 with individual modules 802 inserted into respective individual slots 902.

Wearable assembly 904 may implement wearable assembly 702 and may be configured as headgear and/or any other type of device configured to be worn by a user.

As shown in FIG. 9A, each slot 902 is surrounded by a wall (e.g., wall 906) such that when modules 802 are inserted into their respective individual slots 902, the walls physically separate modules 802 one from another. In alternative embodiments, a module (e.g., module 802-1) may be in at least partial physical contact with a neighboring module (e.g., module 802-2).

Each of the modular assemblies described herein may be inserted into appropriately shaped slots or cutouts of a wearable assembly, as described in connection with FIGS. 9A-9B. However, for ease of explanation, such wearable assemblies are not shown in the figures.

As shown in FIGS. 8 and 9B, modules 802 may have a hexagonal shape. Modules 802 may alternatively have any other suitable geometry (e.g., in the shape of a pentagon, octagon, square, rectangular, circular, triangular, free-form, etc.).

Figure 10:
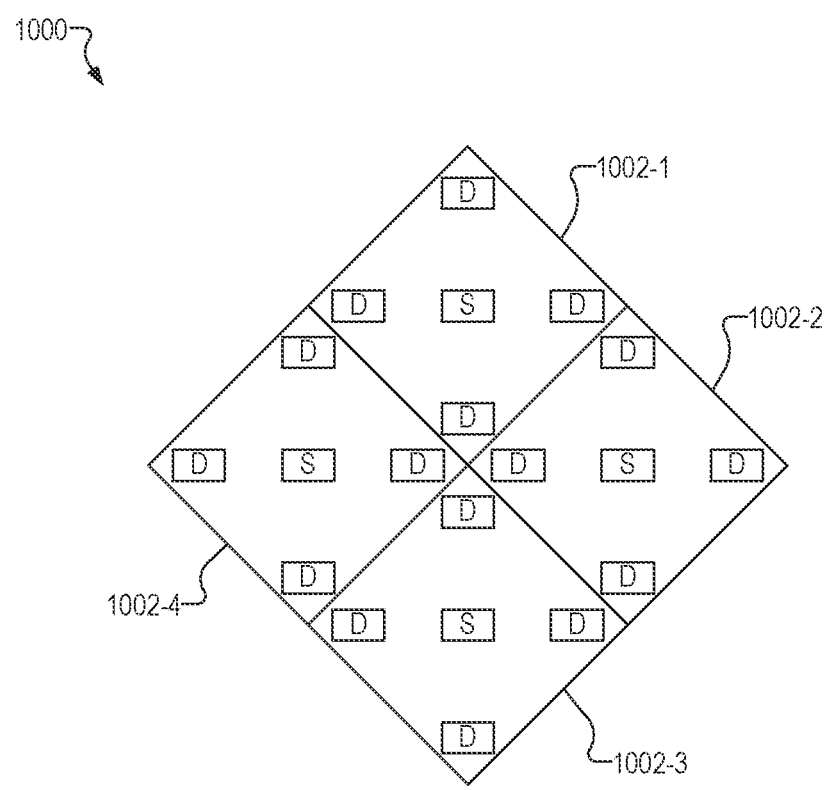

To illustrate, FIG. 10 shows another illustrative modular assembly 1000 that may implement optical measurement system 700. As shown, modular assembly 1000 includes a plurality of modules 1002 (e.g., modules 1002-1 through 1002-4) that are each in the shape of a diamond. While four modules 1002 are shown to be included in modular assembly 1000, in alternative configurations, any number of modules 1002 (e.g., a single module up to sixteen or more modules) may be included in modular assembly 1000.

Modular assembly 1000 is similar to modular assembly 800 in that each module 1002 of modular assembly 1000 includes a light source "S" surrounded by a plurality of detectors "D". In the particular implementation shown in FIG. 10, each module 1002 includes a single light source and four detectors such that a ratio of detectors to light sources in modular assembly 1000 is four to one.

Figure 11:
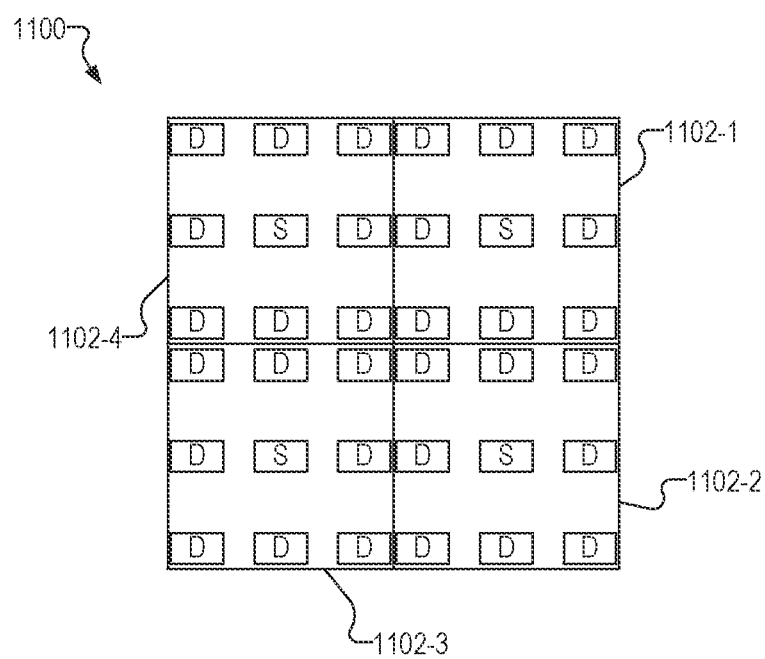

FIG. 11 shows another illustrative modular assembly 1100 that may implement optical measurement system 700. As shown, modular assembly 1100 includes a plurality of modules 1102 (e.g., modules 1102-1 through 1102-4) that are each in the shape of a square. While four modules 1102 are shown to be included in implementation 1100, in alternative configurations, any number of modules 1102 (e.g., a single module up to sixteen or more modules) may be included in modular assembly 1100.

Modular assembly 1100 is similar to modular assembly 800 in that each module 1102 of modular assembly 1100 includes a light source "S" surrounded by a plurality of detectors "D". In the particular implementation shown in FIG. 11, each module 1102 includes a single light source and eight detectors such that a ratio of detectors to light sources in modular assembly 1100 is eight to one.

Figure 12:
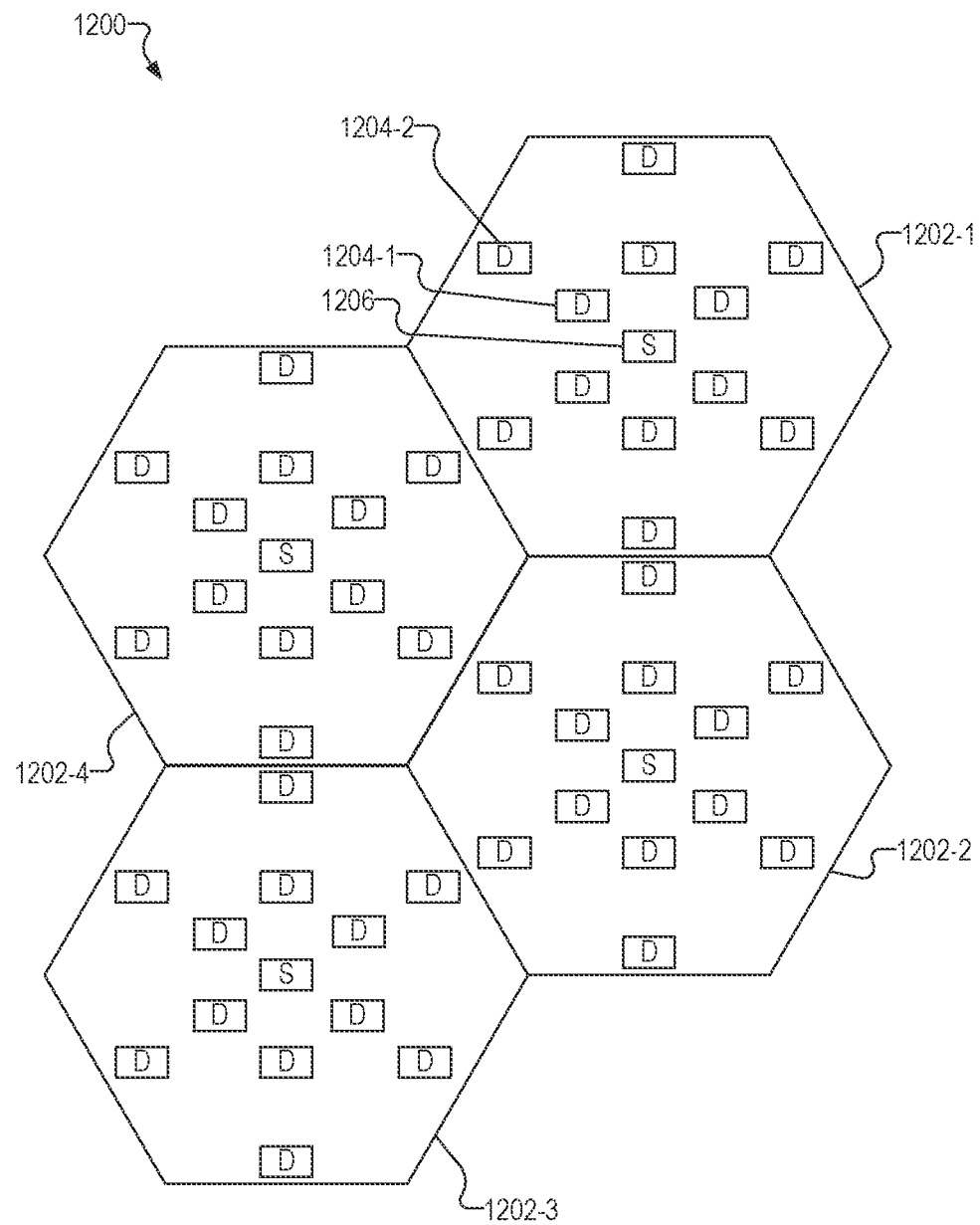

FIG. 12 shows another illustrative modular assembly 1200 that may implement optical measurement system 700. As shown, modular assembly 1200 includes a plurality of modules 1202 (e.g., modules 1202-1 through 1202-4) that are each in the shape of a hexagon. While four modules 1202 are shown to be included in modular assembly 1200, in alternative configurations, any number of modules 1202 (e.g., a single module up to sixteen or more modules) may be included in modular assembly 1200.

Modular assembly 1200 is similar to modular assembly 800 in that each module 1202 of modular assembly 1200 includes a light source "S" surrounded by a plurality of detectors "D". In the particular implementation shown in FIG. 12, each module 1202 includes a single light source and twelve detectors such that a ratio of detectors to light sources in modular assembly 1200 is twelve to one. As shown, some of the detectors (e.g., detector 1204-1) of a module (e.g., module 1202-1) are closer to a light source (e.g., light source 1206) of the module than other detectors (e.g., detector 1204-2) of the same module.

Figure 13:
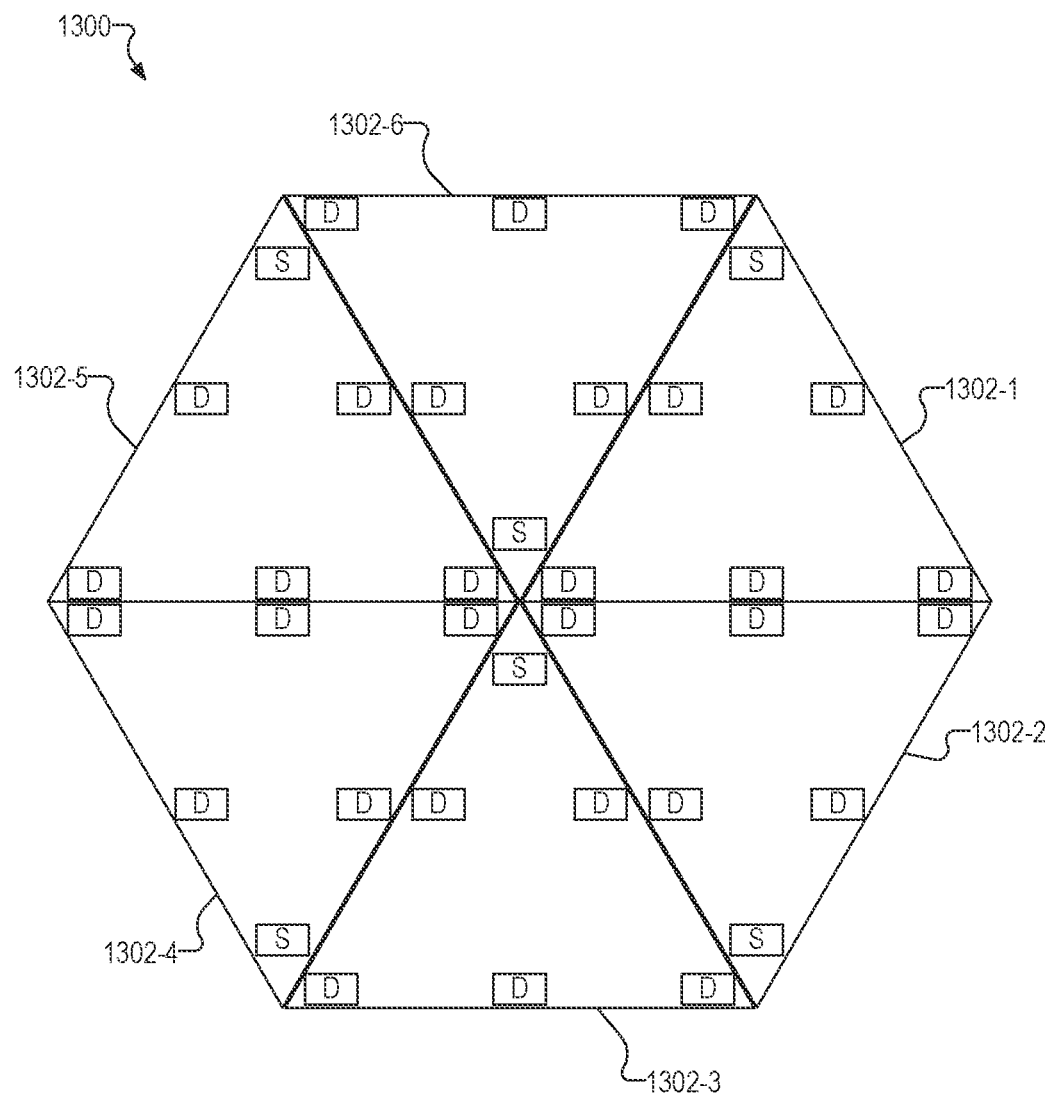

FIG. 13 shows another illustrative modular assembly 1300 that may implement optical measurement system 700. As shown, modular assembly 1300 includes a plurality of modules 1302 (e.g., modules 1302-1 through 1302-6) that are each in the shape of a triangle. While six modules 1302 are shown to be included in modular assembly 1300, in alternative configurations, any number of modules 1302 (e.g., a single module up to sixteen or more modules) may be included in modular assembly 1300.

Modular assembly 1300 is similar to modular assembly 800 in that each module 1302 of modular assembly 1300 includes a light source "S" and a plurality of detectors "D". However, in the particular implementation shown in FIG. 13, the light source for each module 1302 is located away from a center region of the module 1302. For example, the light source for each module 1302 is located towards one of the vertices of the module 1302.

Figure 14:
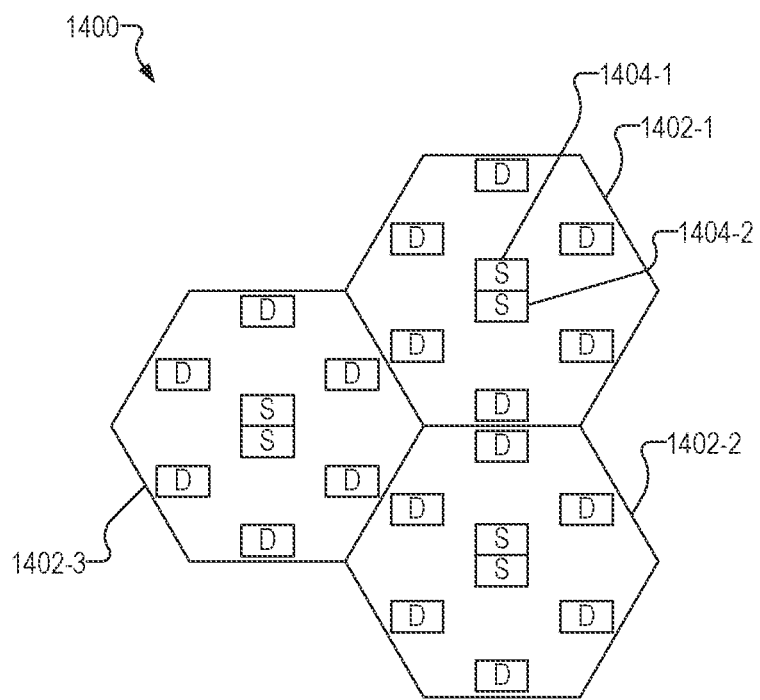

FIG. 14 shows another illustrative modular assembly 1400 that may implement optical measurement system 700. As shown, modular assembly 1400 includes a plurality of modules 1402 (e.g., modules 1402-1 through 1402-4) that are each in the shape of a hexagon. While three modules 1402 are shown to be included in modular assembly 1400, in alternative configurations, any number of modules 1402 (e.g., a single module up to sixteen or more modules) may be included in modular assembly 1400.

Modular assembly 1400 is similar to modular assembly 800, except that in modular assembly 1400 each module 1402 includes two light sources "S" (instead of one light source) and a plurality of detectors "D". For example, module 1402-1 includes a first light source 1404-1 and a second light source 1404-2. As shown, each pair of light sources may be co-located (e.g., right next to each other) on their respective module 1402. In this configuration, light source 1404-1 may emit light having a first wavelength and light source 1404-2 may emit light having a second wavelength different than the first wavelength. Any of the other modular assemblies described herein may include multiple light sources per module as may serve a particular implementation.

The dual light source configuration shown in FIG. 14 may be used when it is desired for an optical measurement system to concurrently measure or detect different properties. For example, pairs of lights sources operating at different wavelengths may be used to measure the concentrations of oxygenated and deoxygenated hemoglobin, which are at different wavelengths.

In each of the modular assemblies described in connection with FIGS. 8-14, a positioning of the modules may cause one or more detectors of a first module to not only detect arrival times for photons of light emitted by a light source of the first module, but to also detect arrival times for photons of light emitted by a light source of a second module.

For example, with reference to modular assembly 800 of FIG. 8, detector 806-3 is located on a side of module 802-1 that is adjacent to module 802-2. As such, detector 806-3 of module 802-1 may be configured to detect photons of light emitted by the light source of module 802-1 and photons of light emitted by the light source of module 802-2. Likewise, detector 810 of module 802-2 may be configured to detect photons of light emitted by the light source 804-2 of module 802-2 and photons of light emitted by the light source of module 802-1. Other detectors (e.g., detectors 806-1, 806-2, and 806-4 through 806-6) may be too far from the light source 804-2 of module 802-2 to detect photons of light emitted by the light source 804-2 of module 802-2.

Figure 15A:
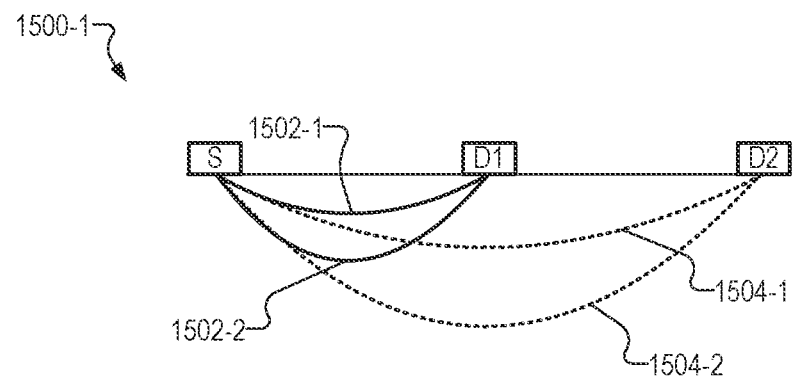
FIGS. 15A-15B illustrate spatial and time dependent optical path regions between a light source and a plurality of detectors.

Such physical positioning of neighboring modules may result in the same light source being included in more than one S-D pair, thereby providing a relatively high effective spatial resolution. For example, FIG. 15A illustrates an exemplary configuration 1500-1 in which a light source (labeled "S") is included in two spatially overlapping S-D pairs. In particular, the light source is included in a first S-D pair with a first detector labeled "D1" and a second S-D pair with a second detector labeled "D2".

FIG. 15A also illustrates a first optical path region (i.e., the region within solid banana path lines 1502-1 and 1502-2) associated with the first S-D pair and a second optical path region (i.e., the region within the dashed banana path lines 1504-1 and 1504-2) associated with the second S-D pair. The first optical path region represents possible spatially-dependent optical paths for photons between the light source S and the first detector D1. Likewise, the second optical path region represents possible spatially-dependent optical paths for photons between the light source S and the second detector D2. As shown, the first and second optical path regions partially overlap, thereby indicating that the first and second S-D pairs are spatially overlapping.

Figure 15B:
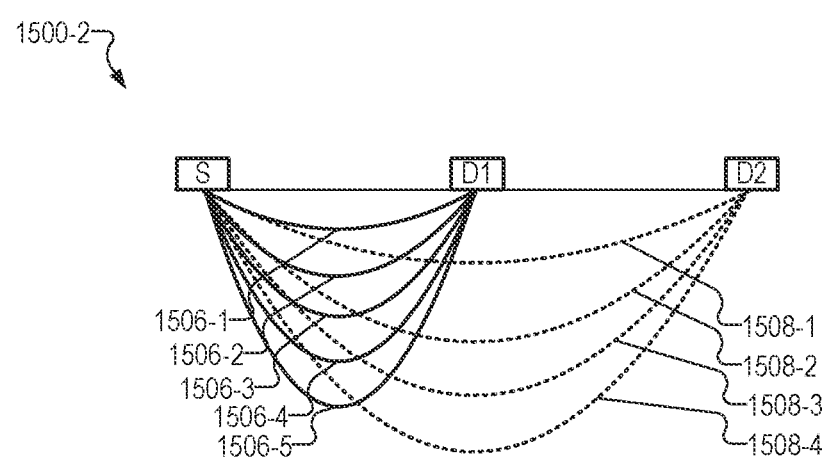

FIG. 15B shows an exemplary configuration 1500-2 in which a time-of-flight measurement technique is used by an optical measurement system that includes the light source S and detectors D1 and D2.

In FIG. 15B, a first plurality of optical path regions (i.e., the regions between solid banana path lines 1506-1 through 1506-5) are associated with the first S-D pair. The first plurality of optical path regions represent possible time-dependent optical paths for photons between the light source S and the first detector D1.

Likewise, a second plurality of optical path regions (i.e., the regions between dashed banana path lines 1508-1 through 1508-4) are associated with the second S-D pair. The second plurality of optical path regions represent possible time-dependent optical paths for photons between the light source S and the second detector D2. As shown, the first and second plurality of optical path regions partially overlap, thereby indicating that the first and second S-D pairs are also temporally overlapping.

As illustrated by FIGS. 15A and 15B, the optical measurement systems described herein provide both spatially and time dependent optical paths between a single light source and a plurality of detectors. In this manner, the optical measurement systems described herein may provide an effective spatial resolution that is relatively high even without a dedicated light source for every detector, as is found in conventional HD DOT systems.

Figure 16A:
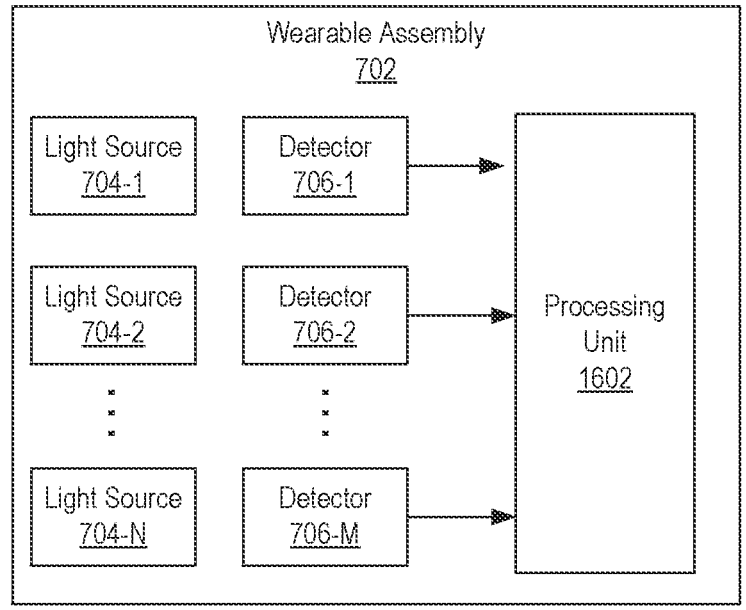
FIGS. 16A-16B show illustrative configurations that include a processing unit.
Figure 16B:
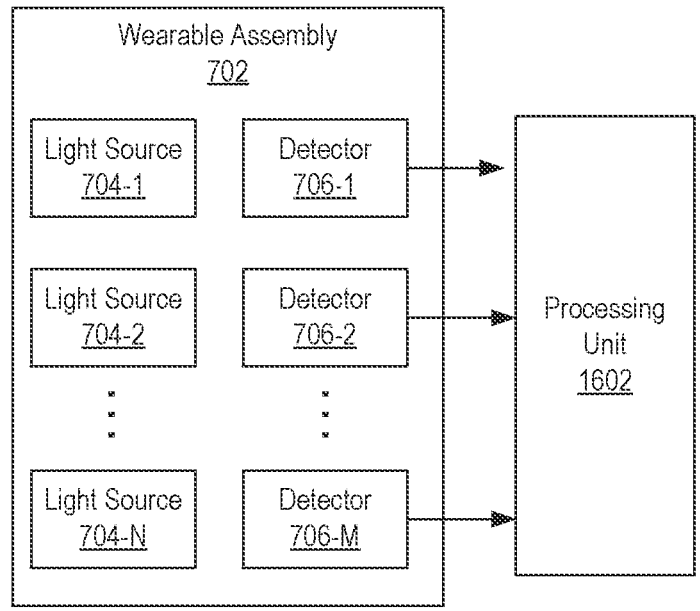

In some examples, the optical measurement systems described herein may further include a processing unit configured to perform one or more operations based on arrival times detected by the detectors described herein. For example, FIGS. 16A-16B show illustrative configurations 1600-1 and 1600-2 in accordance with the principles described herein. Each configuration 1600 includes the wearable assembly 702, light sources 704 and detectors 706 described in connection with FIG. 7. In configuration 1600-1, a processing unit 1602 is also included in wearable assembly 702. In configuration 1600-2, processing unit 1602 is not included in wearable assembly 702 (i.e., processing unit 1602 is located external to wearable assembly). Either configuration 1600-1 or 1600-2 may be used in accordance with the systems, circuits, and methods described herein.

Detectors 706 are configured to output signals representative of photon arrival times, as described herein. Processing unit 1602 is configured to receive the output signals and perform one or more operations based on the signals. For example, processing unit 1602 may generate one or more histograms based on the signals, as described herein.

As mentioned, in configuration 1600-2, processing unit 1602 is not included in wearable assembly 702. To illustrate, processing unit 1602 may be included in a wearable device separate from wearable assembly 702. For example, processing unit 1602 may be included in a wearable device configured to be worn off the head while wearable assembly 702 is worn on the head. In these examples, one or more communication interfaces (e.g., cables, wireless interfaces, etc.) may be used to facilitate wearable assembly 702 and the separate wearable device.

Additionally or alternatively, in configuration 1600-2, processing unit 1602 may be remote from the user (i.e., not worn by the user). For example, processing unit 1602 may be implemented by a stand-alone computing device communicatively coupled to wearable assembly 702 by way of one or more communication interfaces (e.g., cables, wireless interfaces, etc.).

Processing unit 1602 may be implemented by processor 108, controller 112, control circuit 204, and/or any other suitable processing and/or computing device or circuit.

Figure 17:
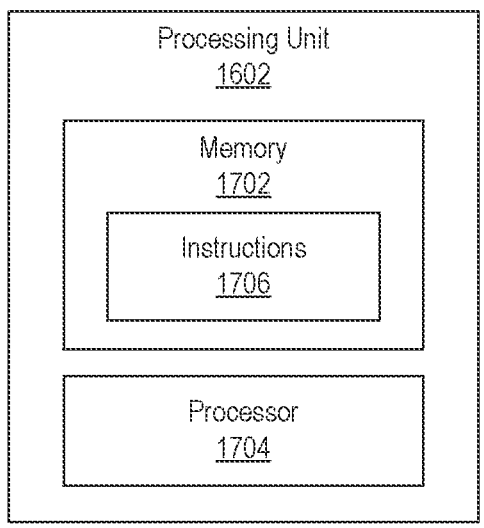
FIG. 17 illustrates an exemplary implementation of a processing unit.

For example, FIG. 17 illustrates an exemplary implementation of processing unit 1602 in which processing unit 1602 includes a memory 1702 and a processor 1704 configured to be selectively and communicatively coupled to one another. In some examples, memory 1702 and processor 1704 may be distributed between multiple devices and/or multiple locations as may serve a particular implementation.

Memory 1702 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1702 may maintain (e.g., store) executable data used by processor 1704 to perform one or more of the operations described herein. For example, memory 1702 may store instructions 1706 that may be executed by processor 1704 to perform any of the operations described herein. Instructions 1706 may be implemented by any suitable application, program (e.g., sound processing program), software, code, and/or other executable data instance. Memory 1702 may also maintain any data received, generated, managed, used, and/or transmitted by processor 1704.

Processor 1704 may be configured to perform (e.g., execute instructions 1706 stored in memory 1702 to perform) various operations described herein. For example, processor 1704 may be configured to perform any of the operations described herein as being performed by processing unit 1602.

FIGS. 18-23 illustrate embodiments of a wearable device 1800 that includes elements of the optical detection systems described herein. In particular, the wearable devices 1800 shown in FIGS. 18-23 include a plurality of modules 1802, similar to any of the modules and module configurations described herein. For example, each module 1802 may include a light source and a plurality of detectors. The wearable devices 1800 may each also include a controller (e.g., controller 112) and a processor (e.g., processor 108) and/or be communicatively connected to a controller and processor. In general, wearable device 1800 may be implemented by any suitable headgear and/or clothing article configured to be worn by a user. The headgear and/or clothing article may include batteries, cables, and/or other peripherals for the components of the optical measurement systems described herein.

Figure 18:
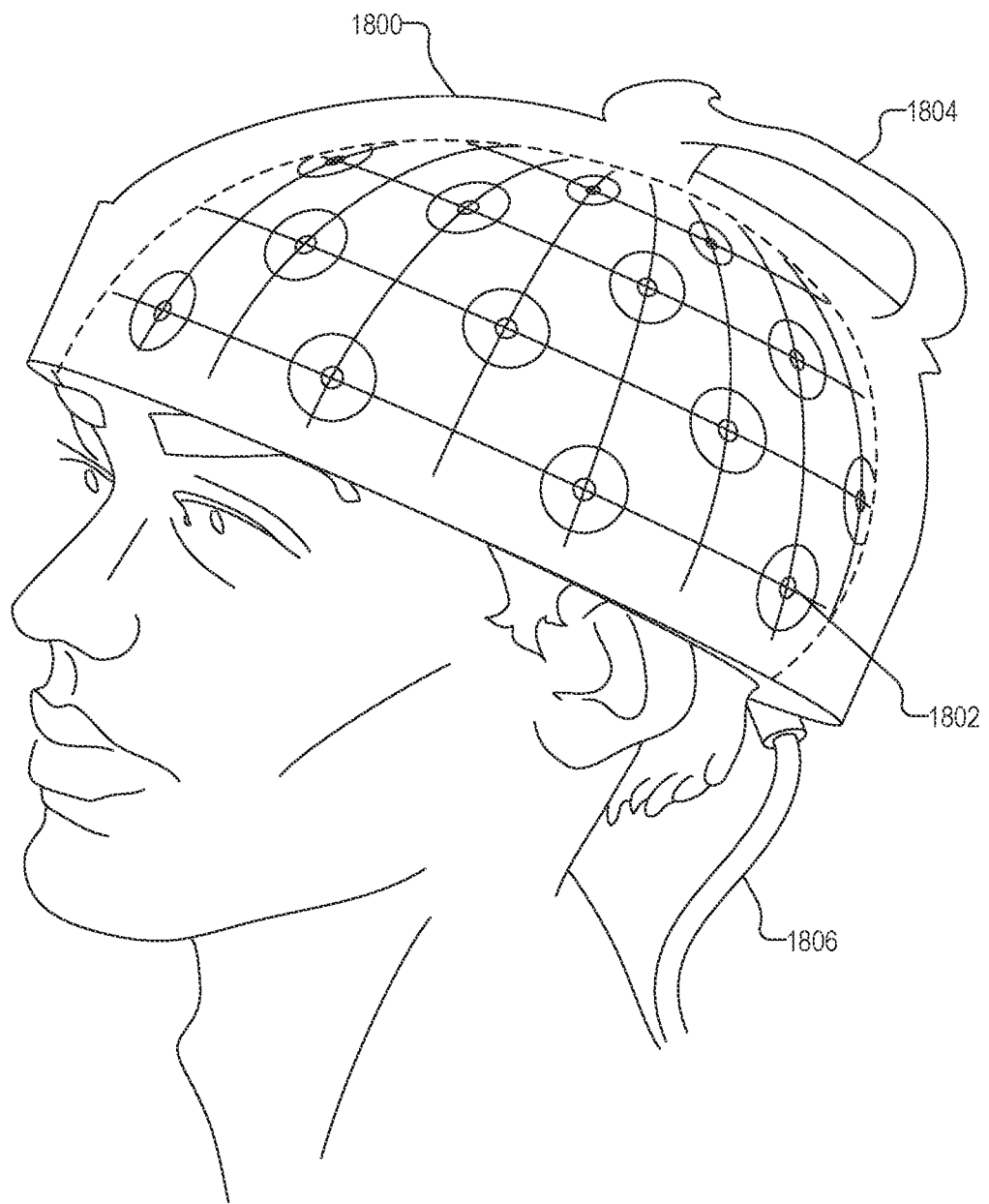
FIGS. 18-23 illustrate embodiments of a wearable device that includes elements of the optical detection systems described herein.
Figure 19:
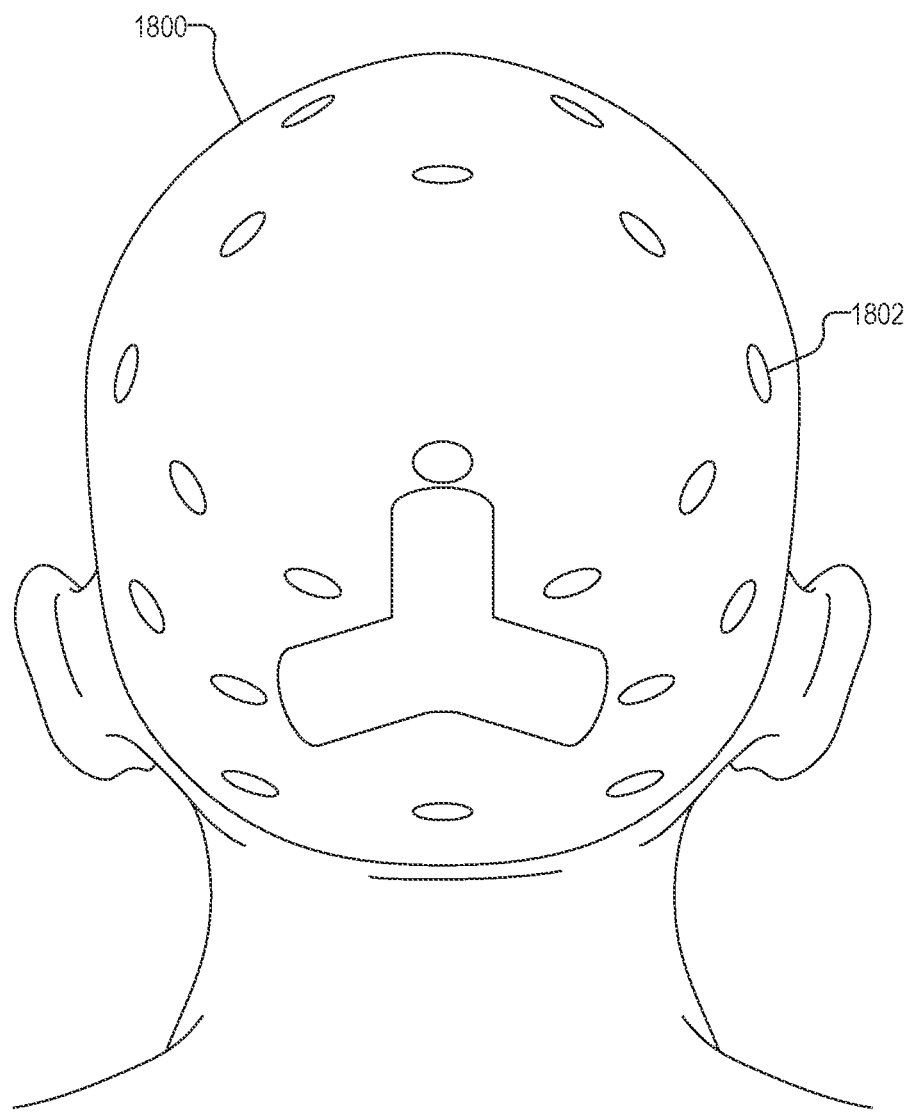
Figure 20:
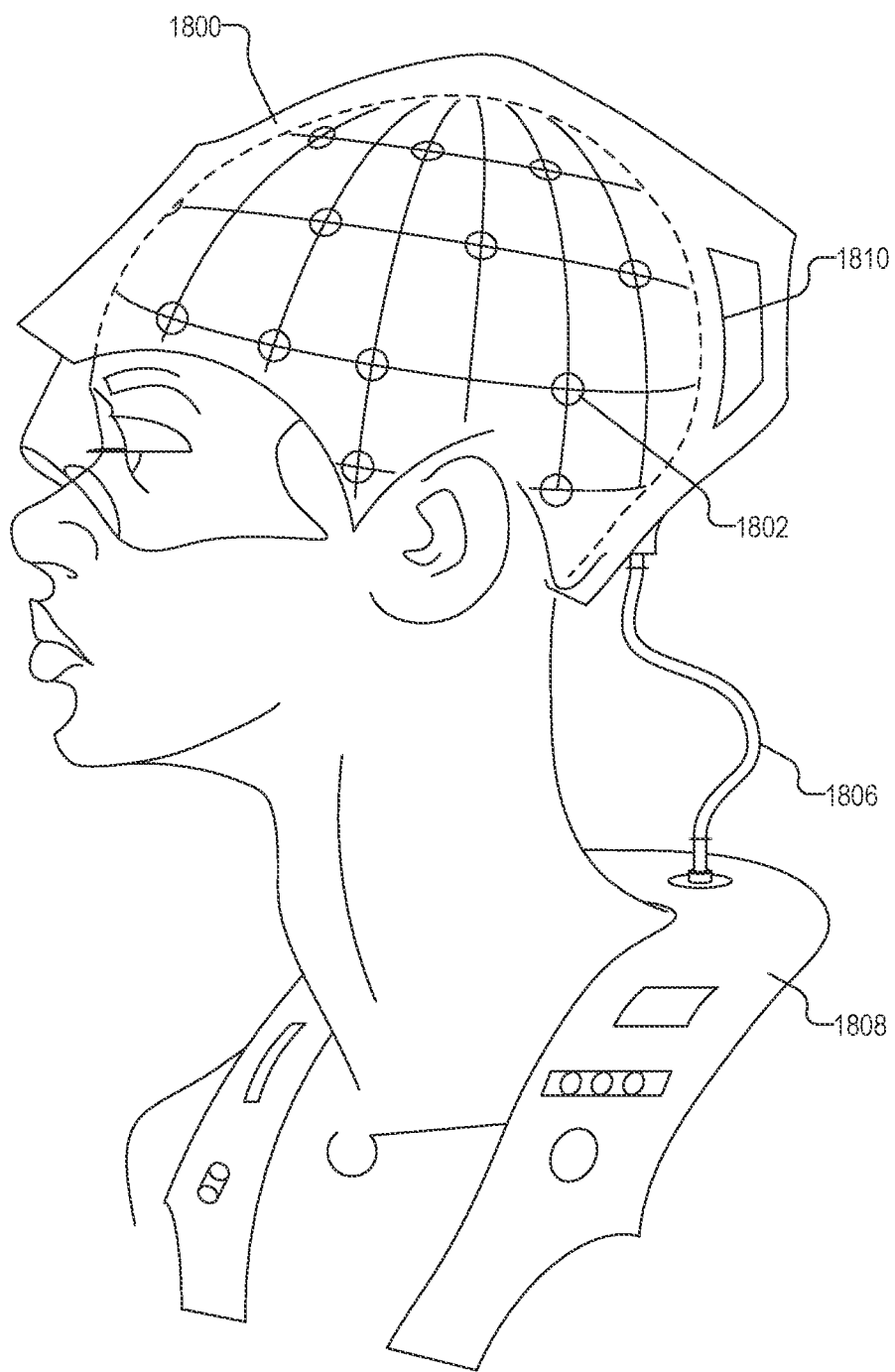

FIG. 18 illustrates an embodiment of a wearable device 1800 in the form of a helmet with a handle 1804. A cable 1806 extends from the wearable device 1800 for attachment to a battery or hub (with components such as a processor or the like). FIG. 19 illustrates another embodiment of a wearable device 1800 in the form of a helmet showing a back view. FIG. 20 illustrates a third embodiment of a wearable device 1800 in the form of a helmet with the cable 1806 leading to a wearable garment 1808 (such as a vest or partial vest) that can include a battery or a hub. Alternatively or additionally, the wearable device 1800 can include a crest 1810 or other protrusion for placement of the hub or battery.

Figure 21:
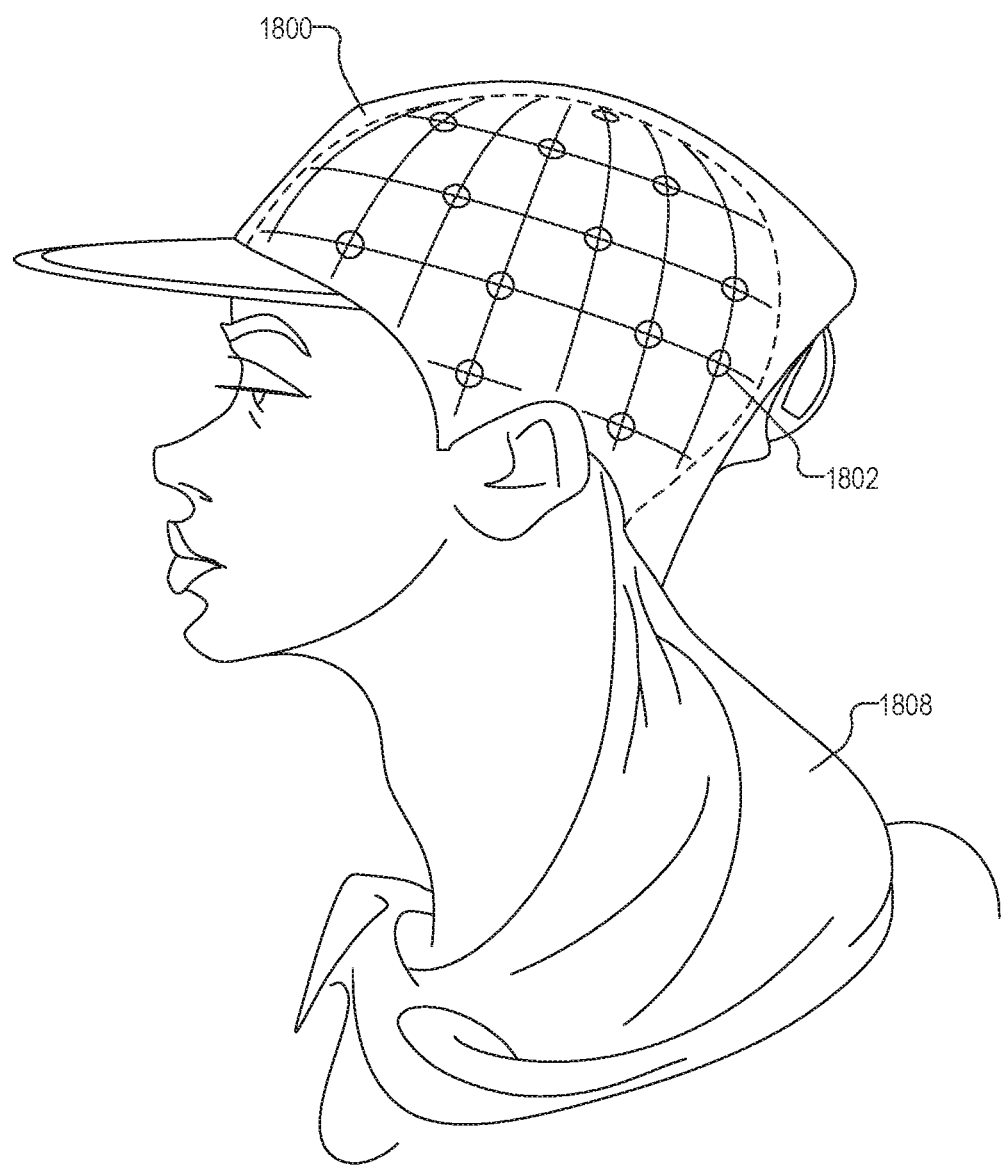
Figure 22:
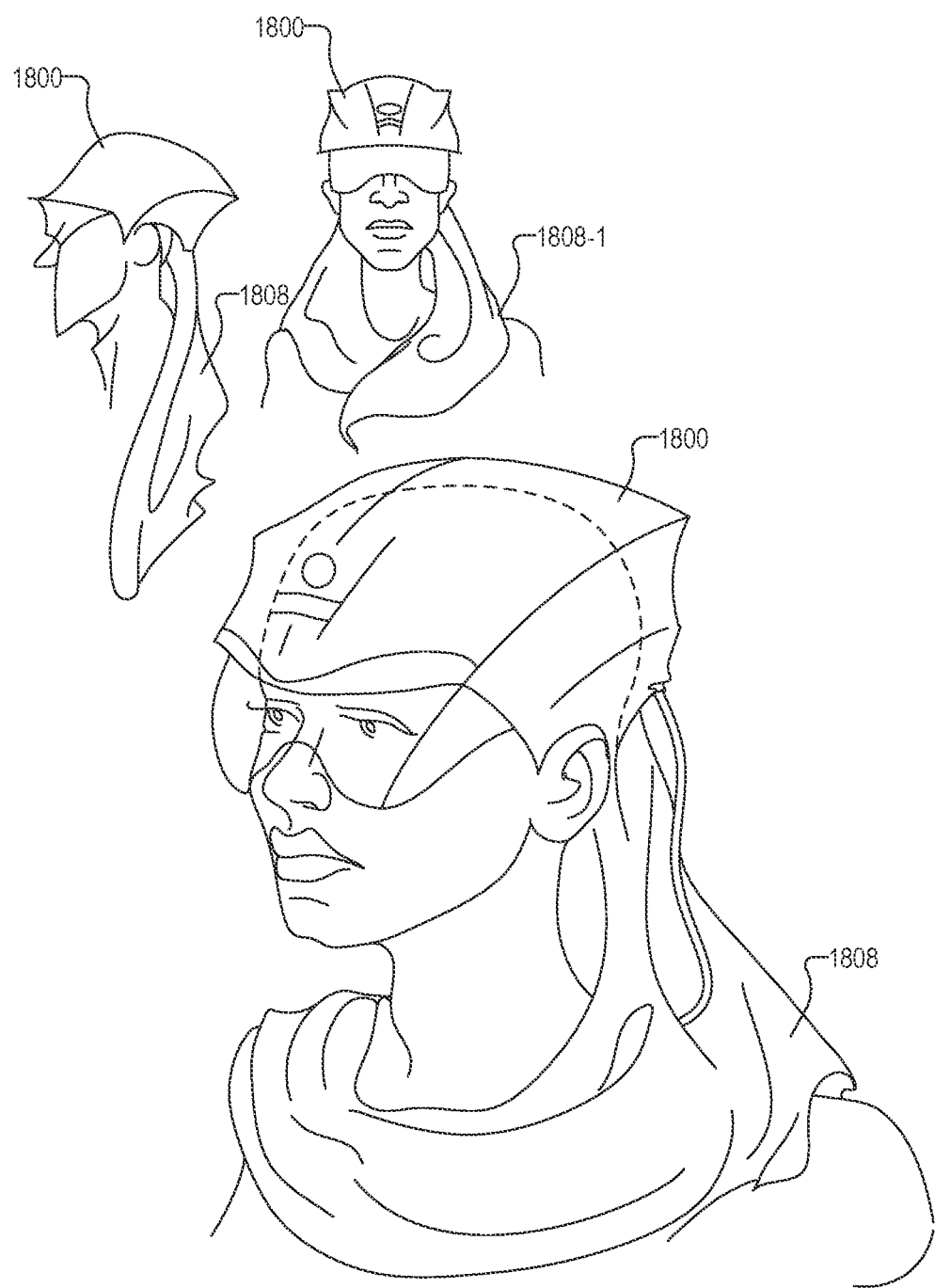
Figure 23:
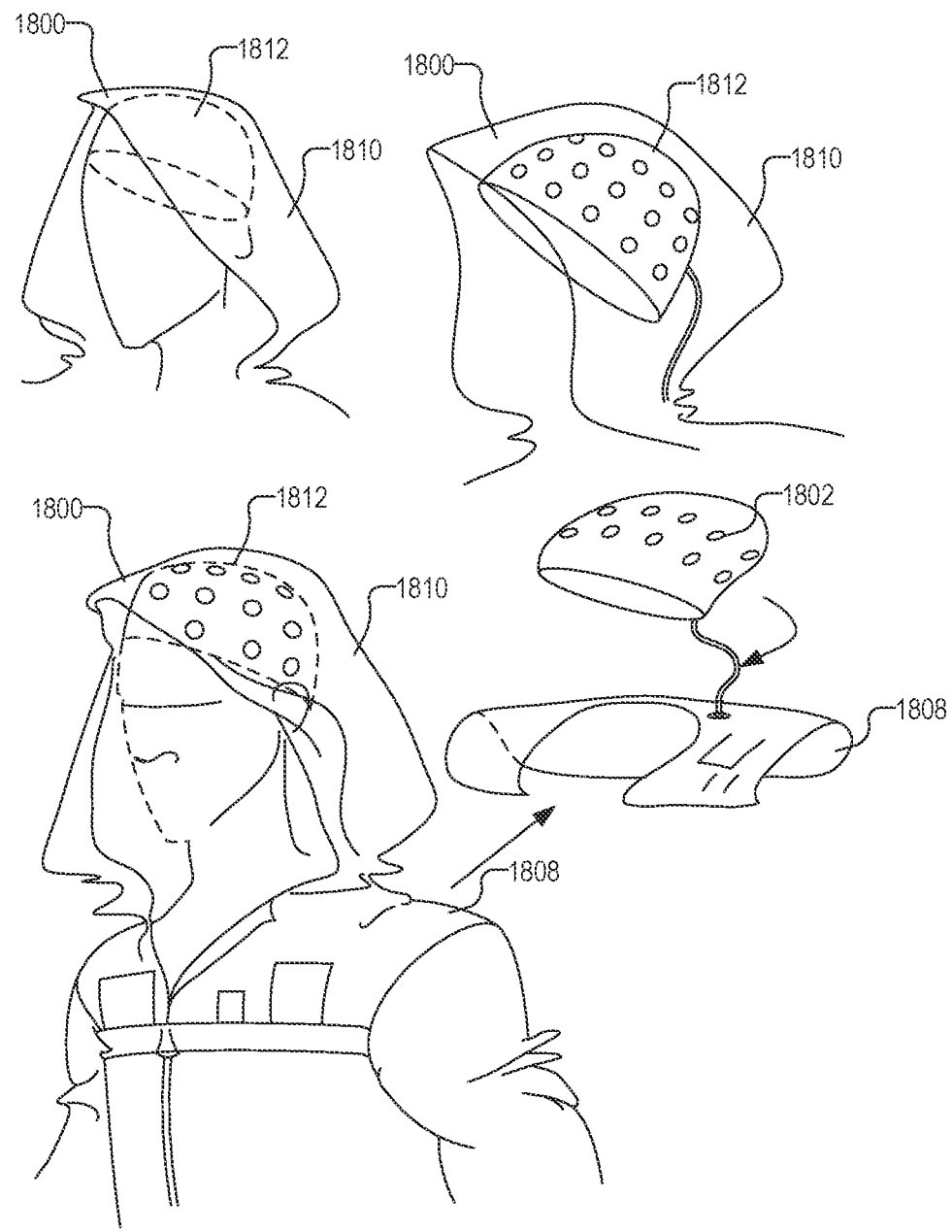

FIG. 21 illustrates another embodiment of a wearable device 1800 in the form of a cap with a wearable garment 1808 in the form of a scarf that may contain or conceal a cable, battery, and/or hub. FIG. 22 illustrates additional embodiments of a wearable device 1800 in the form of a helmet with a one-piece scarf 1808 or two-piece scarf 1808-1. FIG. 23 illustrates an embodiment of a wearable device 1800 that includes a hood 1810 and a beanie 1812 which contains the modules 1802, as well as a wearable garment 1808 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 24:
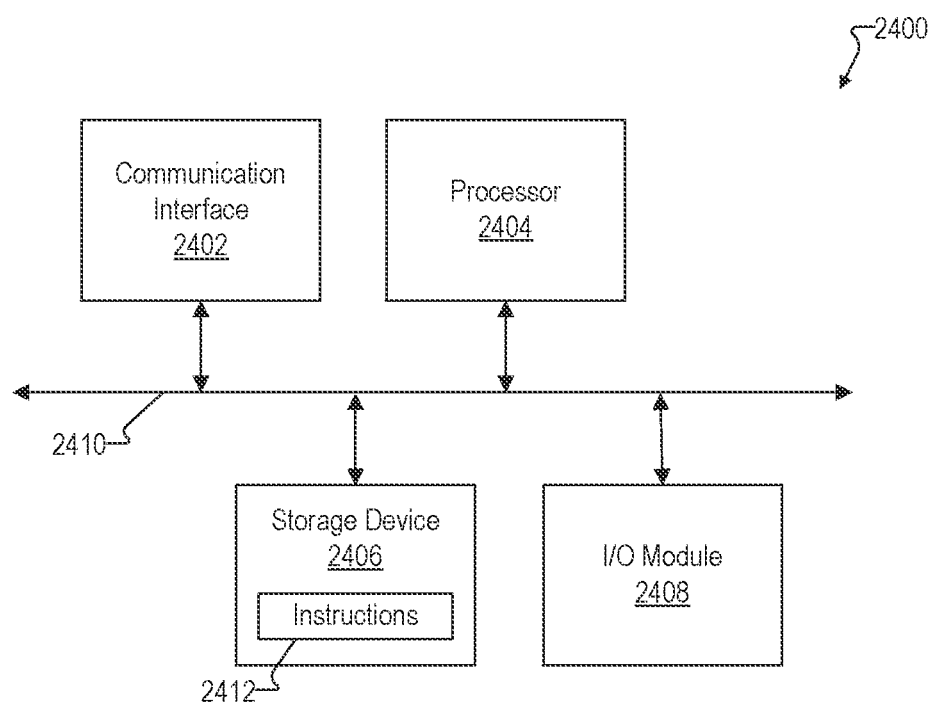
FIG. 24 illustrates an exemplary computing device.

FIG. 24 illustrates an exemplary computing device 2400 that may be specifically configured to perform one or more of the processes described herein. Any of the systems, units, computing devices, and/or other components described herein may be implemented by computing device 2400.

As shown in FIG. 24, computing device 2400 may include a communication interface 2402, a processor 2404, a storage device 2406, and an input/output ("I/O") module 2408 communicatively connected one to another via a communication infrastructure 2410. While an exemplary computing device 2400 is shown in FIG. 24, the components illustrated in FIG. 24 are not intended to be limiting. Additional or alternative components may be used in other embodiments. Components of computing device 2400 shown in FIG. 24 will now be described in additional detail.

Communication interface 2402 may be configured to communicate with one or more computing devices. Examples of communication interface 2402 include, without limitation, a wired network interface (such as a network interface card), a wireless network interface (such as a wireless network interface card), a modem, an audio/video connection, and any other suitable interface.

Processor 2404 generally represents any type or form of processing unit capable of processing data and/or interpreting, executing, and/or directing execution of one or more of the instructions, processes, and/or operations described herein. Processor 2404 may perform operations by executing computer-executable instructions 2412 (e.g., an application, software, code, and/or other executable data instance) stored in storage device 2406.

Storage device 2406 may include one or more data storage media, devices, or configurations and may employ any type, form, and combination of data storage media and/or device. For example, storage device 2406 may include, but is not limited to, any combination of the non-volatile media and/or volatile media described herein.

Electronic data, including data described herein, may be temporarily and/or permanently stored in storage device 2406. For example, data representative of computer-executable instructions 2412 configured to direct processor 2404 to perform any of the operations described herein may be stored within storage device 2406. In some examples, data may be arranged in one or more databases residing within storage device 2406.

I/O module 2408 may include one or more I/O modules configured to receive user input and provide user output. I/O module 2408 may include any hardware, firmware, software, or combination thereof supportive of input and output capabilities. For example, I/O module 2408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2408 is configured to provide graphical data to a display for presentation to a user. The graphical data may be representative of one or more graphical user interfaces and/or any other graphical content as may serve a particular implementation.

An illustrative optical measurement system may include a wearable assembly configured to be worn by a user and comprising a plurality of light sources each configured to emit light directed at a target and a plurality of detectors configured to detect arrival times for photons of the light after the light is scattered by the target, wherein a ratio of a total number of the detectors to a total number of the light sources is at least two to one.

An illustrative optical measurement system may include a headgear configured to be worn on a head of a user and having a plurality of slots; a first module configured to be located in a first slot of the plurality of slots and comprising a first light source configured to emit light directed at a target within the head of the user and a first set of detectors configured to detect arrival times for photons of the light emitted by the first light source; and a second module configured to be located in a second slot of the plurality of slots and comprising a second light source configured to emit light directed at the target within the head of the user, and a second set of detectors configured to detect arrival times for photons of the light emitted by the second light source. A positioning of the first and second modules in the slots of the headgear may be configured to cause one or more detectors of the first set of detectors to also detect arrival times for the photons of the light emitted by the second light source and one or more detectors of the second set of detectors to detect arrival times for the photons of the light emitted by the first light source.

An illustrative optical measurement system may include a plurality of light sources each configured to emit light directed at a target, a plurality of detectors configured to detect arrival times for photons of the light after the light is scattered by the target, wherein a ratio of a total number of the detectors to a total number of the light sources is at least two to one, and a processing unit configured to perform an operation based on the detected arrival times.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
   a wearable assembly configured to be worn by a user and comprising a plurality of modules each configured to fit within a different slot of a plurality of slots of the wearable assembly, the plurality of slots each surrounded by a wall, the plurality of modules including a first module that comprises:
      a first light source and a second light source each configured to emit light directed at a target, and
      a first set of detectors configured to detect arrival times for photons of the light emitted by the first and second light sources after the light emitted by the first and second light sources is scattered by the target;
   wherein
      the first light source is configured to emit light having a first wavelength,
      the second light source is configured to emit light having a second wavelength different than the first wavelength,
      a ratio of a total number of the detectors of the first module to a total number of the light sources of the first module is at least two to one,
      the walls that surround the plurality of slots physically separate the first module from a second module included in the plurality of modules, and
      a positioning of the first and second modules in the slots of the wearable assembly is configured to cause one or more detectors of the first set of detectors to also detect arrival times for photons of light emitted by a third light source included in the second module.

2. The optical measurement system of claim 1, wherein the second module further comprises:
   a fourth light source configured to emit light directed at the target, and
   a second set of detectors configured to detect arrival times for photons of the light emitted by the third and fourth light sources after the light emitted by the third and fourth light sources is scattered by the target.

3. The optical measurement system of claim 2, wherein:
   the third light source is configured to emit light having the first wavelength; and
   the fourth light source is configured to emit light having the second wavelength.

4. The optical measurement system of claim 2, wherein the first and second modules are configured to be removably attached to the wearable assembly.

5. The optical measurement system of claim 2, wherein:
   the positioning of the first and second modules within the wearable assembly causes one or more detectors included in the second set of detectors to detect arrival times for the photons of the light emitted by the first light source.

6. The optical measurement system of claim 1, wherein the first set of detectors includes at least two detectors.

7. The optical measurement system of claim 1, wherein:
   the first light source is located at a center region of a surface of the first module; and detectors included in the first set of detectors are distributed around the first light source on the surface of the first module.

8. The optical measurement system of claim 7, wherein the detectors included in the first set of detectors are all equidistant from the first light source.

9. The optical measurement system of claim 1, wherein the first light source is located away from a center region of a surface of the first module.

10. The optical measurement system of claim 1, further comprising a processing unit configured to perform an operation based on the detected arrival times.

11. The optical measurement system of claim 10, wherein the performing of the operation comprises generating at least one histogram based on the detected arrival times.

12. The optical measurement system of claim 10, wherein the processing unit is included in the wearable assembly.

13. The optical measurement system of claim 10, wherein the processing unit is not included in the wearable assembly.

14. The optical measurement system of claim 1, wherein each detector in the first set of detectors comprises:
   a photodetector configured to generate a photodetector output pulse in response to detecting a photon of the light; and
   a time-to-digital converter configured to record a timestamp symbol in response to an occurrence of the photodetector output pulse, the timestamp symbol representative of an arrival time for the photon.

* * * * *